United States Patent
Kono et al.

(12) 
(10) Patent No.: US 6,392,106 B1
(45) Date of Patent: May 21, 2002

(54) PROCESS FOR PRODUCING 1,1,1,2,2-PENTAFLUOROETHANE

(75) Inventors: Satoru Kono; Toshikazu Yoshimura; Takashi Shibanuma, all of Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/509,989

(22) PCT Filed: Oct. 7, 1998

(86) PCT No.: PCT/JP98/04527

§ 371 Date: Apr. 5, 2000

§ 102(e) Date: Apr. 5, 2000

(87) PCT Pub. No.: WO99/19286

PCT Pub. Date: Apr. 22, 1999

(30) Foreign Application Priority Data

Oct. 9, 1997 (JP) ............................................ 9-276884

(51) Int. Cl.$^7$ .............................................. C07C 17/08
(52) U.S. Cl. ....................... 570/164; 570/165; 570/166; 570/167; 570/168; 570/169
(58) Field of Search ................................ 570/164, 165, 570/166, 167, 168, 169

(56) References Cited

U.S. PATENT DOCUMENTS 5,334,787 A * 8/1994 Felix et al. .................. 570/169

FOREIGN PATENT DOCUMENTS

| JP | 7-324044 | 12/1995 |
|----|----------|---------|
| WO | WO 95/16654 | 6/1995 |
| WO | WO 95/32168 | 11/1995 |
| WO | WO 96/06062 | 2/1996 |

* cited by examiner

Primary Examiner—Alan Siegel
(74) Attorney, Agent, or Firm—Larson & Taylor PLC

(57) ABSTRACT

A process for producing 1,1,1,2,2-pentafluoroethane by fluorinating with hydrogen fluoride at least one of 2,2-dichloro-1,1,1-trifluoroethane and 2-chloro-1,1,1,2-tetrafluoroethane as a starting material, the process being characterized by separating the reaction mixture resulting from the fluorination into a product portion A mainly containing 1,1,1,2,2-pentafluoroethane and a product portion B mainly containing 2,2-dichloro-1,1,1-trifluoroethane, 2-chloro-1,1,1,2-tetrafluoroethane and hydrogen fluoride, removing a fraction mainly containing 2,2-dichloro-1,1,1,2-tetrafluoroethane from the product portion B, and recycling the rest of the product portion B as part of feedstocks for fluorination.

According to the process of the invention, the amount of CFC-115 contained in the target HFC-125 can be remarkably reduced through a simplified procedure.

4 Claims, 1 Drawing Sheet

PROCESS FOR PRODUCING 1,1,1,2,2-PENTAFLUOROETHANE

TECHNICAL FIELD

The present invention relates to a process for producing 1,1,1,2,2-pentafluoroethane (HFC-125).

BACKGROUND ART 1,1,1,2,2-pentafluoroethane (HFC-125), which is a useful hydrofluorocarbon compound for its zero ozone depleting potential, is used in applications such as refrigerant, foaming agent, solvent, propellant and dry-etchant.

Among known processes for producing HFC-125, U.S. Pat. No. 3,755,477 discloses a process comprising fluorinating perchloroethylene or 2,2-dichloro-1,1,1-trifluoroethane (HCFC-123), and U.S. Pat. No. 5,334,787 discloses a process comprising fluorinating 2,2-dichloro-1,1,1-trifluoroethane (HCFC-123) or 2-chloro-1,1,1,2-tetrafluoroethane (HCFC-124).

These processes produce, in addition to the target HFC-125, various compounds as impurities including chlorofluoroethanes (CFCs) such as 1,2,2-trichrolo-1,1,2-trifluoroethane (CFC-113), 2,2,2-trichrolo-1,1,1-trifluoroethane (CFC-113a), 1,2-dichrolo-1,1,2,2-tetrafluoroethane (CFC-114), 2,2-dichrolo-1,1,1,2-tetrafluoroethane (CFC-114a), 2-chrolo- 1,1,1,2,2-pentafluoroethane (CFC-115), etc.; 2-chrolo-1,1,1-trifluoroethane (HCFC-133a) and 1,1,1,2-tetrafluoroethane (HFC-134a). Further, when HCFC-123 is used as a starting material, part of HCFC-123 is fluorinated to form HCFC-124. Whereas, when HCFC-124 is used as a starting material, HCl produced therein as a by-product reacts with the unreacted HCFC-124 to produce HCFC-123.

Among these compounds, HCFC-123 and HCFC-124 can be converted into the target HFC-125 by fluorination; therefore, in the case where a single gas-phase reactor is used for fluorination, they are economically recycled together with the unreacted HF, and fed to the reactor to be reused as starting materials together with newly added HCFC-123 or HCFC-124.

On the other hand, among the impurities, CFC-115 and HFC-134a respectively have a boiling point close to that of the target HFC-125; therefore, they are prone to be contained in HFC-125 when separating HFC-125 from the reaction mixture. HFC-125 needs to be highly purified in order to be used in the above-mentioned applications; however, the separation of CFC-115 is difficult in the subsequent purifying process of HFC-125, and the separation can not be achieved by way of a usual distillation process, whereby disadvantageously causing purity degradation and low yield of HFC-125. It is necessary to conduct a special distillation process such as an extractive distillation to effect sharp separation of CFC-115 from HFC-125 (Japanese Unexamined Pat. Publication No. 3082/1996). The separation of CFC-115 thus necessitates additional apparatuses for extractive distillation and the like, which leads to increased costs of equipment and production.

Furthermore, in the case of reusing HCFC-123, HCFC-124, HF and the like as the feedstocks, CFCs such as CFC-113, 113a, 114 and 114a are contained in the feedstocks and converted to CFC-115 as a result of a further fluorination in a reactor, thereby increasing the amount of CFC-115 contained in the reaction products.

Among known processes for the preparation of HFC-125 by using HCFC-124 as a starting material with reduced production of CFCs, U.S. Pat. No. 5,475,167 discloses a process which uses $Cr_2O_3$ as a catalyst, whereby the amount of CFC-115 relative to HFC-125 is regulated to about 0.1–0.5%. However, since the process employs particular $Cr_2O_3$ catalyst pre-treated with CO, $H_2$ or $H_2O$, the pre-treatment of catalyst is necessarily conducted to cause the process to be complicated. Moreover, HCFC-124 and HF in the process continuously flow and react together in the reactor and HCFC-123, HCFC-124, HF and the like are not reused as feedstocks; therefore, if the reaction products are recycled, fluorination of CFCs contained in the reaction products would be promoted to increase the production ratio of CFC-115.

WO95/16654 discloses a process for producing HFC-125 which comprises the steps of fluorinating perchloroethylene to produce HCFC-122, HCFC-123 or HCFC-124, removing CFCs such as CFC-112, 113 and 114 from the reaction product, and then further fluorinating the reaction product. However, since, according to this process, HFC-125 is produced by two-step fluorination of perchloroethylene used as the starting material, it is impossible to know how to reduce the production of CFC-115 in a process wherein a single gas-phase reactor is used for fluorination and the reaction products are recycled.

DISCLOSURE OF INVENTION

A primary object of the present invention is to provide a process for producing HFC-125 by fluorinating HFCF-123 and/or HCFC-124 as a starting material with HF and reusing CFC-123, HCFC-124 and HF in the reaction mixture as feedstocks for fluorination, wherein the production of CFC-115, which is a product difficult to be separated from HFC-125, can be reduced.

The inventors conducted an extensive study considering the above-mentioned problems in the prior art. As a result, the inventors found that, in the process for producing HFC-125 by fluorinating HCFC-123 and/or HCFC-124 as a starting material with HF and recycling HCFC-123, HCFC-124 and HF as feedstocks for fluorination, the impurities such as CFCs including CFC-113, 113a, 114, 114a and the like are mostly isomerized or fluorinated products of CFC-113a which is formed as a result of dismutation of HCFC-123, and that, because CFC-113, CFC-113a and the like among the impurities are very quickly fluorinated, most of the CFCs turn to CFC-114a when a steady state is reached, i.e., when the composition of reaction mixture is substantially fixed during the continuous reaction. The inventors also found that the amount of CFCs present in the recycled materials can be effectively decreased by separating the fluorinated reaction mixture into a portion mainly containing HFC-125 and a portion mainly containing HCFC-123, HCFC-124 and HF, removing a fraction mainly containing CFC-114a from the latter portion, and recycling the residual part of the latter portion as part of feedstocks for the continuous fluorinating reaction. Based on the above findings, the present invention was accomplished, which is capable of remarkably reducing the amount of CFC-115 contained in the target HFC-125.

Thus, the invention provides a process for producing 1,1,1,2,2-pentafluoroethane as described below.

(1) a process for producing 1,1,1,2,2-pentafluoroethane (HFC-125) by fluorinating with hydrogen fluoride at least one of 2,2-dichloro-1,1,1-trifluoroetahne (HCFC-123) and 2-chloro-1,1,1,2-tetrafluoroethane (HCFC-124) as a starting material, the process being characterized by separating the reaction mixture resulting from the fluorination into a product portion A mainly containing 1,1,1,2,2-pentafluoroethane (HFC-125) and a product portion B mainly containing 2,2-dichloro-1,1,1-trifluoroethane (HCFC-123), 2-chloro-1,1,1,2-tetrafluoroethane (HFCF-124) and hydrogen fluoride (HF), removing a fraction mainly containing 2,2-dichloro-1,1,1,2-tetrafluoroethane (CFC-114a) from the product portion B, and recycling the rest of the product portion B as part of feedstocks for fluorination.

(2) a process according to the item 1, wherein the method of separating the reaction mixture resulting from the fluorination into the product portion A mainly containing 1,1,1,2,2-pentafluoroethane and the product portion B mainly containing 2,2-dichloror-1,1,1-trifluoroethane, 2-chloro-1,1,1,2-tetrafluoroethane and hydrogen fluoride is a partial condensation of the reaction mixture, using a heat exchanger, for giving a non-condensate mainly containing 1,1,1,2,2-pentafluoroethane and a condensate mainly containing 2,2-dichloro-1,1,1-trifluoroethane, 2-chloro-1,1,1,2-tetrafluoroethane and hydrogen fluoride.

(3) a process according to the item 1 or 2, wherein the method of removing the fraction mainly containing 2,2-dichloro-1,1,1,2-tetrafluoroethane from the product portion B is a method of distilling the product portion B and withdrawing the fraction from the middle section of a distillation column.

(4) a process according to the item 2 or 3, wherein the product portion B is introduced into a separation tank to obtain a liquid phase A mainly comprising hydrogen fluoride and a liquid phase B mainly comprising 2,2-dichloro-1,1,1-trifluoroethane and 2-chloro-1,1,1,2-tetrafluoroethane, and recycling the liquid phase A as part of the feedstocks for fluorination while only the liquid phase B is subjected to the distillation.

The process for producing HFC-125 of the invention is a process comprising fluorinating at least one of HCFC-123 and HCFC-124 as the starting material with hydrogen fluoride (HF) in the gas phase to obtain HFC-125.

Type of the reactor to be used in the fluorination reaction is not critical, and a tubular reactor or fluidized bed reactor, for example, may be used. In addition, a heat insulating type reactor or thermal control type reactor may be used in the invention.

In the fluorination reaction, a known catalyst having fluorinating activity such as chromium oxide, chromium fluoride, fluorinated chromium oxide, aluminum fluoride, fluorinated aluminum oxide or the like may be used. Further, a metal or metals (for example, Zn, Ni, In, Cr, etc.) may be added to the above catalyst. The catalyst may be used as supported on a known carrier such as activated carbon.

Reaction conditions in the fluorination are not limited and may be suitably selected depending on the level of catalyst activity. Typically, the reaction pressure may preferably be at about 0–10 kg/cm$^2$, more preferably about 0.5–4 kg/cm$^2$. The reaction temperature may preferably be at about 200–400° C., more preferably at about 250–350° C. The proportion of gaseous hydrogen fluoride (HF) used for fluorination to at least one of HCFC-123 and HCFC-124 used as the starting material is preferably about 1.5–10, more preferably about 2–in terms of the mixing ratio (by mole) of HF/starting material (at least one of HCFC-123 and HCFC-124), at the inlet of the reactor.

The contact time in the reactor, expressed as catalyst weight/volumetric feed rate of feedstocks gas (HCFC-123, HCFC-124 and HF), may preferably be about 1–20 gr·s/cc, more preferably about 1–5 gr·s/cc.

The reaction mixture thus obtained contains HCFC-123, HCFC-124, HF, HCl and the like as the unreacted starting materials or reaction products and CFCs as the impurities in addition to the target HFC-125.

The reaction mixture is then separated into the product portion A containing the target HFC-125 and the product portion B mainly containing HCFC-123, HCFC-124 and HF. The separation may preferably be conducted by partial condensation using a partial condenser such as a heat exchanger since HFC-125 is remarkably low in the boiling point when compared to HCFC-123, HCFC-124, HF and the like; in the partial condensation process, the reaction mixture is partially condensed to give a non-condensate portion (product portion A) mainly containing HFC-125 and HCl and a condensate portion (product portion B) containing HCFC-123, HCFC-124 and HF. The partial condensation pressure may preferably be about 0–10 kg/cm$^2$, more preferably about 0.5–4 kg/cm$^2$. The partial condensation temperature may preferably be about –30 to 40° C., more preferably about –20 to 30° C. To effectively carry out the partial condensation, heat exchangers having different cooling temperatures may be used in combination.

The product portion A containing HCF-125 is subjected to purification processes such as acid elimination, dehydration, fractionation, etc. to obtain the target HCF-125.

The product portion B contains CFCs such as CFC-113, 113a, 114, and 114a as impurities in addition to HCFC-123, HCFC-124 and HF which can be reused as the feedstocks. These CFCs are mostly isomerized or fluorinated products of CFC-113a which is formed as a result of dismutation of HCFC-123, and most of the CFCs turn to CFC-114a when a steady state is reached, i.e., when the composition of reaction mixture is substantially fixed during the continuous reaction, because CFC-113, CFC-113a and the like among the impurities are very quickly fluorinated. Therefore, in the present invention, when recycling HCFC-123, HCFC-124 and HF, the fraction mainly containing CFC-114a is removed from the product portion B. According to the process, the CFCs content in the product portion B is reduced highly effectively.

The fraction mainly containing CFC-114a can be easily removed from the product portion B by distillation. Specifically, the fraction having a high concentration of CFC-114a condenses on trays positioned at the middle section of a distillation column; therefore, the fraction can be easily removed from the product portion B by withdrawing the fraction on the trays at the middle section of the distillation column from the column. The distillation may preferably be conducted at a pressure of about 0–10 kg/cm$^2$, more preferably about 3–8 kg/cm$^2$. The condensation temperature in the condenser at the top of the distillation column may be in the range of –20 to 40° C.

The fraction obtained at the middle section of the distillation column usually contains CFC-114, HCFC-123, HCFC-124, etc. in addition to CFC-114a. Therefore, as required, the fraction may be subjected to a further distillation to increase the concentrations of CFC-114 and CFC-114a so as to remove them from the system, thereby enabling to use HCFC-123 and HCFC-124 more effectively.

The non-condensate at the top of the distillation column mostly comprises HFC-125; therefore, it is preferred to subject the non-condensate, together with the product portion A, to the purification steps such as acid elimination, dehydration, fractionation or the like so as to recover the target HFC-125.

The reflux during the distillation is a mixture mainly comprising HCFC-124 and HF, while the bottom product and substances having relatively high boiling points in the distillation column are mixtures mainly comprising HCFC- 123. Since the reflux, bottom product and high boiling point substances can be useful feedstocks for the fluorination reaction, they are recirculated to the gas-phase fluorination reactor to be reused as part of the feedstocks.

When the HCFC-123 concentration is high and the HF concentration is low in the product portion B, the product portion B is prone to separate into a phase rich in HF and a phase rich in organic substances such as HCFC-123 and HCFC-124. In this case, when so required, the product portion B may be cooled and supplied to a separation tank prior to the above-described distillation operation so as to be separated into a liquid phase A mainly comprising HF and a liquid phase B mainly comprising HCFC-123 and HCFC-124. The liquid phase A can be reused as part of feedstocks for the fluorination reaction. The liquid phase B is subjected to the above-described distillation operation to remove the fraction mainly comprising CFC-114a therefrom. In these treatments, the concentration of HF in the liquid phase A is usually about 80 mol % or higher while the concentrations of HCFC-123 and HCFC-124 in the liquid phase B are usually about 80 mol % or higher, whereby the distillation operation can be simplified since only the liquid phase B substantially free of HF is distilled.

The present invention provides an improvement in the process for continuous preparation of HFC-125 by fluorinating at least one of HCFC-123 and HCFC-124 as starting material and recycling the CFC-123, HCFC-124 and HF in the reaction mixture for use as part of the starting materials. According to the invention, the amount of CFC-115 contained in the target HFC-125 can be remarkably reduced through a simplified procedure.

The amount of CFC-115 contained in the obtained HFC-125 varies depending on the manufacturing conditions, but usually is remarkably lowered to 0.5% or below, whereby enabling to effectively produce HFC-125 of high purity.

BEST MODE FOR CARRYING OUT THE INVENTION

Figure 1:
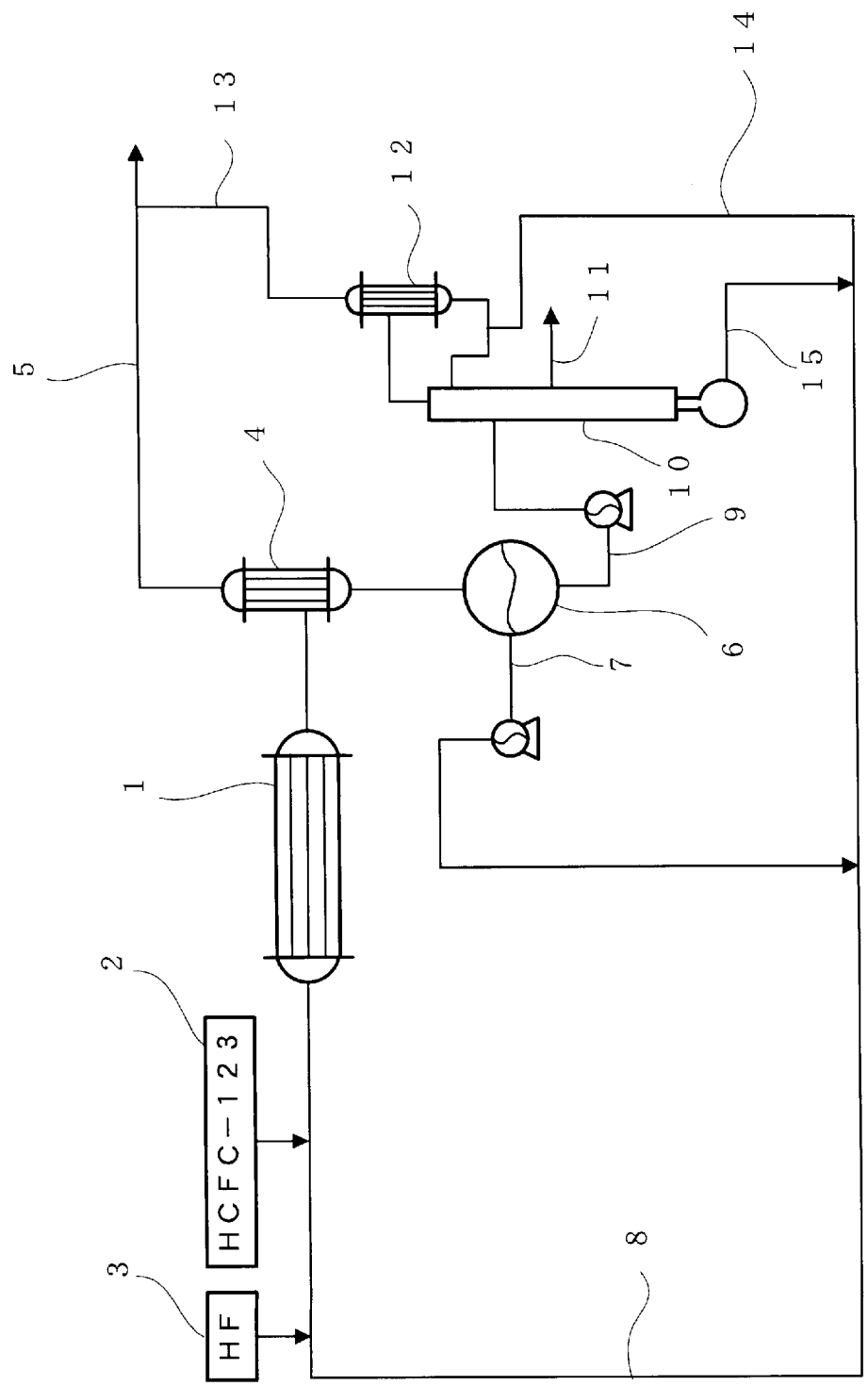
FIG. 1 is a flow chart illustrating one embodiment of the present invention. The reference numerals in FIG. 1 denote as follows. 1: a gas-phase fluorination reactor, 2 and 3: feedstock vessels, 4: a partial condenser, 5, 7, 8, 9, 11, 13, 14 and 15: pipings, 6: a separation tank, 10: a distillation column, and 12: a condenser.

An example of the invention is hereinafter described with reference to the embodiment shown in FIG. 1.

EXAMPLE 1

First, the gas-phase fluorination reactor 1 is charged with 45 kg of fluorinated chromium oxide which is used as a fluorinating catalyst, and to the reactor 1 were fed HCFC-123 from the feedstock vessel 2 at a feed rate of 49 mol/hr and anhydrous HF from the feedstock vessel 3 at a feed rate of 102 mol/hr. The fluorination reaction temperature and the pressure in the reactor 1 were 320° C. and 3.2 kg/cm$^2$, respectively.

Next, a reaction mixture collected from the reactor 1 was introduced into the partial condenser (heat exchanger) 4, and the reaction mixture was partially condensed to give a non-condensate and a condensate at a temperature of −20° C. and at a pressure of 3.1 kg/cm$^2$. The non-condensate mainly comprising HFC-125 was fed to a purification process via the piping 5 and purified to give the target HFC-125. The condensate was sent to the separation tank 6 to be separated into a liquid phase mainly comprising HF and a liquid phase mainly comprising HCFC-123 and HFCF-124. The liquid phase mainly comprising HF was re-supplied to the reactor 1 from the piping 8 via the piping 7. The liquid phase mainly comprising HCFC-123 and HFCF-124 was introduced into the distillation column 10 via the piping 9 to be distilled at a pressure of 7.2 kg/cm$^2$.

Since a fraction containing CFC-114a at a high concentration condensed in the middle section of the distillation column 10, the fraction was removed from the reaction system via the piping 11. The non-condensate in the condenser 12 at the top of the distillation column 10 mainly comprising HFC-125 was fed to the purification process via the piping 13 and purified together with the above-mentioned non-condensate obtained at the condenser 4 to give the target HFC-125. HCFC-124 that was included in the HFC-125 was returned to the distillation column 10.

The reflux in the distillation column 10 and the bottom product in the distillation column 10 were introduced respectively via the piping 14 and the piping 15 into the piping 8, and then fed to the reactor 1 together with the liquid phase separated in the separation tank 6 and mainly comprising HF, to be employed as part of the feedstocks for the fluorination reaction together with HCFC-123 and HF newly supplied.

The temperatures and pressures in the above operations are shown in Table 1. Also, the temperatures and pressures of the reflux and bottom product are shown in Table 1. The pressures are respectively indicated as a gauge pressure.

TABLE 1

| | Temperature (° C.) | Pressure (kg/cm$^2$) |
| --- | --- | --- |
| Fluorination Reactor 1 | 320 | 3.2 |
| Partial Condenser 4 | −20 | 3.1 |
| Separation Tank 5 | −20 | 3.1 |
| Distillation Column 9 | — | 7.2 |
| Reflux | 34 | 7.2 |
| Bottom Product | 70 | 7.2 |

When the above-described operation was continued for 60 hours, compositions of the products were substantially constant. The compositions (flow rate:mol/hr) of the collected product (via the pipings 5 and 13), components to be reused (collected via pipings 7, 14 and 15) and the removed portion from the distillation column (collected via the piping 11) are shown in Table 2.

TABLE 2

| | HFC-125 | HCFC-124 | CFC-114a | HCFC-123 | CFC-115 | HF | HCl |
| --- | --- | --- | --- | --- | --- | --- | --- |
| Collected Product | 49 | 20 | — | — | 0.1 | 4 | 98 |
| Components to be Reused | 6 | 129 | 0.3 | 90 | — | 671 | — |
| Removed Portion | — | 0.5 | 0.5 | 1.5 | — | — | — |

As is apparent from the above results, the ratio of CFC-115 to HFC-125 in the collected product via the pipings 5 and 13 is about 2000 ppm, which is remarkably lowered.

Comparative Example 1

Except for omitting the step of removing the fraction having a high concentration of CFC-114a from the middle section of the distillation column, HFC-125 was produced following the procedure in Example 1. The compositions (flow rate:mol/hr) of the collected product (via the pipings 5 and 13), components to be reused (collected via pipings 7, 14 and 15) and the removed portion from the distillation column (collected via the piping 11) after 60 hours from the start of the reaction are shown in Table 3.

TABLE 3

|  | HFC-125 | HCFC-124 | CFC-114a | HCFC-123 | CFC-115 | HF | HCl |
|---|---|---|---|---|---|---|---|
| Collected Product | 49 | 20 | — | — | 0.6 | 4 | 98 |
| Components to be Reused | 6 | 130 | 1.8 | 88 | — | 671 | — |
| Removed Portion | — | — | — | — | — | — | — |

As is apparent from the above results, in the case where the removal of the fraction having a high concentration of CFC-114a is omitted, the ratio of CFC-115 to HFC-125 in the collected product via pipings 5 and 13 is about 1.2%, which shows a large increase in the content of CFC-115 in comparison with the case where the fraction having a high concentration of CFC-114a is removed.

What is claimed is:

1. A process for producing 1,1,1,2,2-pentafluoroethane by fluorinating with hydrogen fluoride at least one of 2,2-dichloro-1,1,1-trifluoroethane and 2-chloro-1,1,1,2-tetrafluoroethane as a starting material, the process comprising:

separating the reaction mixture resulting from the fluorination into a product portion A mainly containing 1,1,1,2,2-pentafluoroethane and a product portion B mainly containing 2,2-dichloro-1,1,1-trifluoroethane, 2-chloro-1,1,1,2-tetrafluoroethane and hydrogen fluoride, removing a fraction mainly containing 2,2-dichloro-1,1,1,2-tetrafluoroethane from the product portion B, and recycling the rest of the product portion B as part of feedstocks for fluorination.

2. A process according to claim 1, wherein the method of separating the reaction mixture resulting from the fluorination into the product portion A mainly containing 1,1,1,2,2-pentafluoroethane and the product portion B mainly containing 2,2-dichloro-1,1,1-trifluoroethane, 2-chloro-1,1,1,2-tetrafluoroethane and hydrogen fluoride is a partial condensation of the reaction mixture, using a heat exchanger, for giving a non-condensate mainly containing 1,1,1,2,2-pentafluoroethane and a condensate mainly containing 2,2-dichloro-1,1,1-trifluoroethane, 2-chloro-1,1,1,2-tetrafluoroethane and hydrogen fluoride.

3. A process according to claim 1, wherein the method of removing the fraction mainly containing 2,2-dichloro-1,1,1,2-tetrafluoroethane from the product portion B is a method of distilling the product portion B and withdrawing the fraction from the middle section of a distillation column.

4. A process according to claim 2, wherein the product portion B is introduced into a separation tank to obtain a liquid phase A mainly comprising hydrogen fluoride and a liquid phase B mainly comprising 2,2-dichloro-1,1,1-trifluoroethane and 2-chloro-1,1,1,2-tetrafluoroethane, and recycling the liquid phase A as part of the feedstocks for fluorination while only the liquid phase B is subjected to the distillation.

* * * * *